United States Patent [19]
Aretz et al.

[11] Patent Number: 5,714,348
[45] Date of Patent: Feb. 3, 1998

[54] OXYGEN-DEPENDENT FERMENTATION OF MICROORGANISMS

[75] Inventors: Werner Aretz, Königstein; Philipp Willems, Waldems, both of Germany

[73] Assignee: Hoechst Aktiengesellschaft, Frankfurt am Main, Germany

[21] Appl. No.: 700,052

[22] Filed: Aug. 20, 1996

Related U.S. Application Data

[63] Continuation of Ser. No. 335,380, Nov. 3, 1994, abandoned.

[30] Foreign Application Priority Data

Nov. 5, 1993 [DE] Germany .................. 43 37 787.4

[51] Int. Cl.⁶ .................. C12P 21/06; C12P 21/04; C12N 9/14; C12N 1/20
[52] U.S. Cl. .................. 435/69.1; 435/71.1; 435/195; 435/252.8; 435/260
[58] Field of Search .................. 435/252.8, 813, 435/818, 260, 69.1, 71.1, 195; 424/93.2

[56] References Cited

U.S. PATENT DOCUMENTS

| | | | |
|---|---|---|---|
| 3,850,753 | 11/1974 | Chibata et al. | 195/109 |
| 4,048,017 | 9/1977 | Roesler | 195/109 |
| 4,326,035 | 4/1982 | Gabellieri | 435/247 |
| 4,399,221 | 8/1983 | Schneider et al. | 435/193 |
| 4,654,215 | 3/1987 | Yamada et al. | 435/818 |
| 4,692,414 | 9/1987 | Yamada et al. | 435/818 |

FOREIGN PATENT DOCUMENTS

| | | | |
|---|---|---|---|
| A-1278619 | 6/1972 | European Pat. Off. | |
| A-144474 | 6/1985 | European Pat. Off. | |
| A-196061 | 10/1986 | European Pat. Off. | |
| A-504798 | 9/1992 | European Pat. Off. | |
| A-1953430 | 4/1970 | Germany | |
| A-159011 | 2/1983 | Germany | |
| 0290212 | 5/1991 | Germany | 435/252.8 |
| 0595441 | 2/1978 | Sweden | 435/818 |
| A-297444 | 1/1992 | United Kingdom | |

OTHER PUBLICATIONS

Derwent Abstract of DD-A-159011, see abstract 1981.
R. Gherna et al., *Catalogue of Bacteria and Phages*, American Type Culture Collection, 18th Ed., pp. 135, 137 (1992).

*Primary Examiner*—David M. Naff
*Assistant Examiner*—Deborah K. Ware
*Attorney, Agent, or Firm*—Finnegan, Henderson, Farabow, Garrett & Dunner, L.L.P.

[57] ABSTRACT

The present invention relates to a growth-coupled fed-batch fermentation of oxygen-dependent microorganisms. It has been found that oxygen-dependent microorganisms can be advantageously fermented if the carbon supply is carried out as a function of the oxygen uptake rate.

11 Claims, 2 Drawing Sheets

OXYGEN-DEPENDENT FERMENTATION OF MICROORGANISMS

This application is a continuation of application Ser. No. 08/335,380, filed Nov. 3, 1994, now abandoned.

FIELD OF THE INVENTION

The present invention relates to a growth-coupled fed-batch fermentation of oxygen-dependent microorganisms.

BACKGROUND ART

In order to obtain good biomass and product yield in the fermentation of microorganisms, it has until now been necessary to use an empirically determined optimum fermentation procedure, the fermentation parameters in each case having to be newly adjusted by the "trial and error" method on changing the boundary conditions (inoculation method, composition of the fermentation broth, temperature etc.) and the optimum fermentation procedure often not being achieved.

Surprisingly, a fermentation procedure of oxygen-dependent microorganisms has now been found which independently of various fermentation parameters leads to optimum results if the carbon supply of the microorganism takes place as a function of the oxygen uptake rate. This is particularly surprising, because the carbon supply is problematic in the case of oxygen-dependent microorganisms. Thus e.g. an oversupply of the microorganism with glycerol leads to an accumulation thereof, which results in the formation of acetate, growth stoppage and the cessation of product formation.

SUMMARY OF THE INVENTION

The subject of the invention is accordingly a fermentation of oxygen-dependent microorganisms, which comprises the carbon supply of the microorganism in the fermentation broth taking place as a function of the oxygen uptake rate (OUR).

The fermentation according to the invention can be employed for various purposes and it has particular importance in the production of proteins, in particular of recombinant proteins.

According to the present invention, differing microorganisms can be fermented, such as e.g. microorganisms of the genus Escherichia, Streptomyces, Bacillus or Pseudomonas.

Bacteria of the genus Escherichia are particularly suitable for the fermentation according to the invention. The species *Escherichia coli* is very particularly suitable. Of this, the strains W 3110 M (ATCC 27325), DH 1 (ATCC 33849), K 12, B, HB 101, JM105, TG 1, MRC 1, RH1, IH 1776 have particular importance. The strains W 3110 M and DH 1 have very particular importance. The particular importance of the abovementioned strains results inter alia from the fact that they can be optimally fermented (as recipient strains) after modification by genetic engineering with the aim of expressing specific substances. For example, the process is suitable for the production of proteins such as glutaryl acylase, insulin, interferons, hirudin, erythropoietin etc.

The process according to the invention has particular importance in the production of glutaryl acylase, e.g. by expressing the plasmid pCM 145 (DSM 6409) (cf. EP 0 504 798 A1, to which reference is expressly made) in a microorganism (e.g. *E. coli*, in particular W 3110 M, DH 1).

Differing substances are suitable as carbon supply media and a particularly suitable substrate is glycerol. The other nutrients correspond in composition and concentration to those of customary fermentation aids; particularly suitable compositions are shown in the examples (cf. also e.g. Molecular Cloning, Sambrook, Fritsch, Maniatis, Cold Spring Laboratory Press, 1989).

The fermentation according to the present invention can be carried out at different temperatures. In the case of *Escherichia coli*, the preferred temperature is about 28° C. A particular advantage of the present invention, however, is that the fermentation can also be carried out at higher or lower temperature (e.g. 22° to 37° C.) without all the fermentation parameters having to be adjusted. The carbon supply is adjusted quasi-automatically via the detection of the oxygen uptake rate and the determination of the threshold values concerned.

The carbon supply takes place in the fermentation procedure according to the invention by the supply initially taking place proportionally to the oxygen uptake rate until it reaches a threshold value to be determined empirically. A constant supply with the carbon source then takes place until the fermentation is finished; the level of the constant supply must likewise be determined empirically. As a rule, the main production phase in the case of recipient strains modified by genetic engineering starts after the start of the constant supply.

It is particularly advantageous to carry out the supply described in a computer-controlled manner. A particularly suitable algorithm reads as follows:

Basic formula: $SF=(Flag1<1)\times(OUR_{act}/K)+(Flag1\times K_{prod})$

Auxiliary variable 1: $Flag1=[(Flag1>0)+(OUR_{act}>OUR_{opt})+((OUR_{act}<OUR_{min})\times Flag2)]>0$ Auxiliary variable 2: $Flag2=[(Flag2>0)+(OUR_{act}>(OUR_{min}+5))]>0$ Said algorithm applies universally; the values given subsequently in brackets apply by way of example particularly for the microorganism W 3110 M. Said abbreviations have the following meaning:

SF=pump rate (ml/l·h)

Flag1=switch which switches off the OUR-dependent pump rate of the first growth phase and switches on the constant pump rate of the production phase (logical question with the result 1=right or 0=wrong; at the start of fermentation this switch is set to 0; as soon as $OUR_{act}$ is set greater than $OUR_{opt}$ or Flag2 and $OUR_{act}$ is smaller than $OUR_{min}$, Flag1 is set)

Flag2=switch which is set to 0 at the start of fermentation; as soon as $OUR_{act}$ is greater than ($OUR_{min}+5$), Flag2 is set and remains set up to the end K=pump constant=$OUR_{max}/K_{prod}$ (17.5 as an example here)

$OUR_{act}$=growth-dependent, actual oxygen uptake rate $OUR_{max}$=threshold value of the oxygen uptake rate (preferably 60 to 200, particularly preferably 80 to 160, in particular 100 to 140 mmol/l·h; 120 mmol/l·h as an example here)

$OUR_{opt}$=temperature-dependent optimum oxygen uptake rate (preferably 60 to 200, particularly preferably 80 to 160, in particular 90 to 120 mmol/l·h; 120 mmol/l·h as an example here at a fermentation temperature of 28° C., 90 mmol/l·h at a fermentation temperature of 25° C.)

$OUR_{min}$=minimum oxygen uptake rate (see Flag2) (50 to 90 mmol/l·h, 70 mmol/l·h as an example here at a fermentation temperature of 28° C.)

$K_{prod}$=pump rate during production phase (6.85 ml/l·h), preferably 4 to 9, particularly preferably 5 to 8, in particular 6.5 to 7.5 ml/l·h; 6.85 ml/l·h as an example here)

Using the algorithm described, a growth-dependent carbon supply is guaranteed independently of the quality of the inoculum and of the fermentation temperature. The process according to the invention functions with a fermentation in which the inoculation is carried out using a preculture; however, it is also possible to carry out a direct inoculation, which is to he regarded as a particular advantage of the process according to the invention.

The determination of the abovementioned parameters is carried out—as already mentioned—empirically. It is to be taken into account here that the carbon supply must remain below a threshold value at which no carbon oversupply takes place. At a supply rate just under this threshold value, the optimum supply is obtained in the first growth phase by means of the above algorithm. After reaching the threshold value, switching is carried out with the aid of the above algorithm to a lower substantially constant pump rate (i.e. ±10% of the basic value). The magnitude of the constant pump rate is likewise to be determined empirically. The measurement of the oxygen uptake rate is preferably carried out by balancing the discharge of oxygen from the fermenter with the respective introduction using standard measuring equipment.

Figure 1:
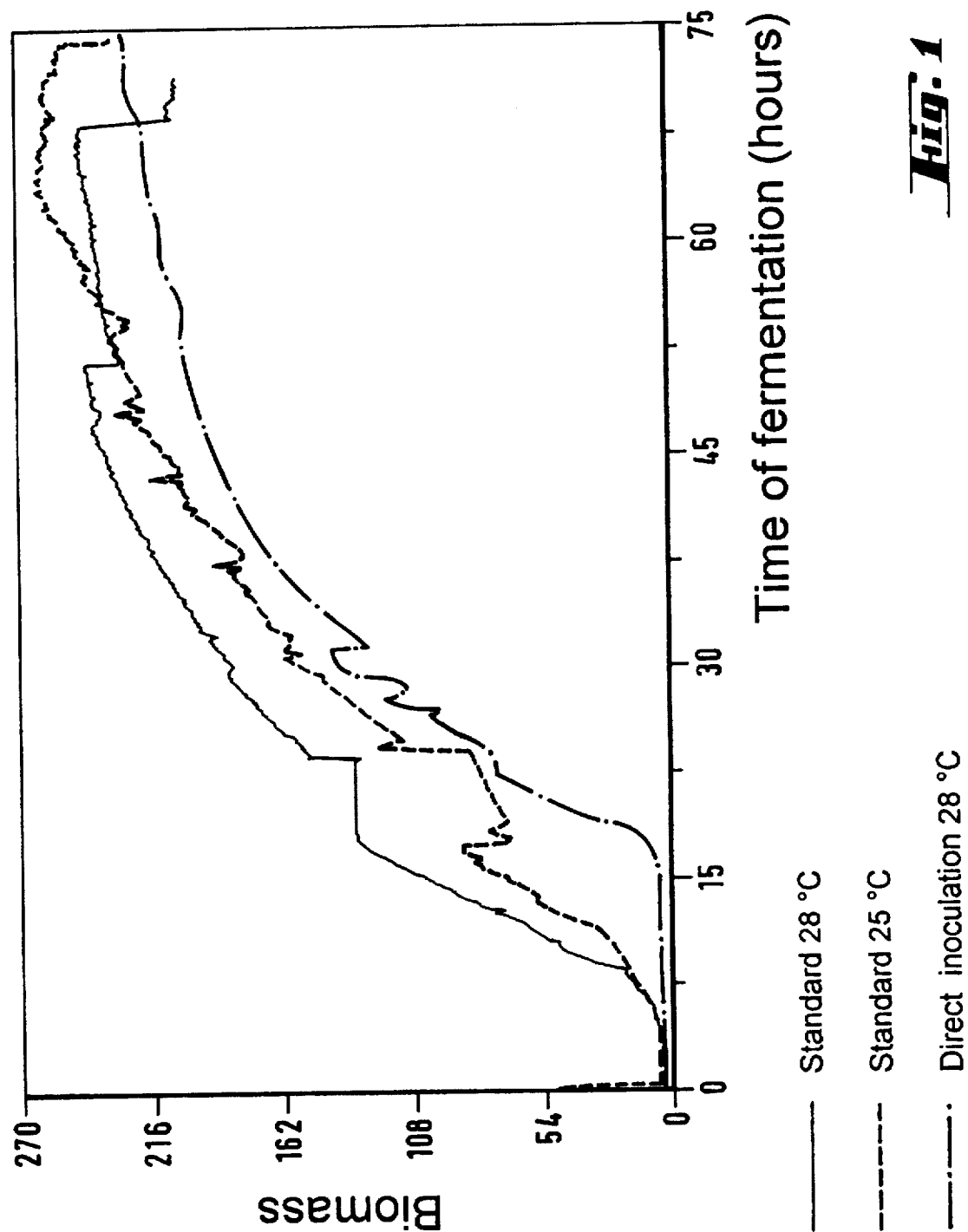
FIGS. 1 and 2: Results of fermentation proceeding automatically under optimum conditions.

The present invention is illustrated in greater detail by the following exemplary embodiments and by the contents of the patent claims.

DESCRIPTION OF THE PREFERRED EMBODIMENTS

EXAMPLE 1

Culture conditions

Culture is carried out under the following conditions:

The *E. coli* strains W 3110 M and DH 1 are incubated in the following medium overnight

| Yeast extract | 0.7% |
|---|---|
| Bactotryptone | 0.4% |
| NaCl | 0.4% |
| Chloramphenicol | 10 µg/ml | and the cultures are then treated with glycerol (final conc. 15%).

From the suspensions, agar plates of the same medium are prepared and incubated for 24 hours at 28° C., and the precultures (PC) inoculated with a single colony.

| PC medium: | |
|---|---|
| Tryptone | 2.0% |
| Yeast extract | 1.0% |
| NaCl | 0.5% |
| Chloramphenicol | 10 µg/ml |
| pH = 7.2 | |

100 ml of these nutrient solutions in 300 ml Erlenmeyer flasks are incubated after inoculation for 16 to 24 hours at 28° C. and 220 rpm. The culture then shows an $OD_{578nm}$ of 6.0 to 8.0.

The following main cultures (MC) are inoculated with 5% of these PC (based on PC having $OD_{578nm}$=3.0):

MC: 40.0 g/l of yeast extract (Oxoid)

1.2 g/l of $NaH_2PO_4 \times H_2O$ 8.5 g/l of $Na_2HPO_4 \times 2H_2O$ 1.0 g/l of KCl 2.0 g/l of $MgSO_4 \times 7H_2O$ 1.0 g/l of citric acid 5.0 g/l of $NH_4Cl$ 4.0 ml/l of trace element solution 0.25 g/l of $CoCl_2 \cdot 6 H_2O$ 0.01 g/l of $NiCl_2 \cdot 6 H_2O$ 0.01 g/l of $CuCl_2 \cdot 2 H_2O$ 0.1 g/l of $ZnCl_2$ 0.5 g/l of $H_3BO_3$ 0.3 g/l of $Na_2MoO_4 \cdot 2 H_2O$ 0.1 g/l of $NaSeO_3 \cdot 3 H_2O$ 0.2 g/l of $SeSO_4 \cdot 7 H_2O$ 0.58 g/l of $MgSO_4 \cdot 7 H_2O$ 0.05 g/l of EDTA adjusted to pH 2 to 3 with HCl)

0.005 g/l of thiamine→sterile-filtered (5 mg/10 ml→0.5/ 50 ml NI)

®Desmophen (polyols, Bayer AG, Leverkusen) pH=6.5

A direct inoculation of the fermenter using only one colony is likewise possible without loss of activity.

Ferm. cond.: Temp.: 28° C. (exception see temperature experiment)

Vol.: 3.5 l vvm: 0.75 constant rpm: 500 to 1200 (r=7 cm)

pH: 7.0±0.2 (keep constant using 25% strength $NH_4OH$/ 1M $H_3PO_4$)

Fed-batch: Glycerol solution: 525 g of glycerol (99%)/l of MC medium (without $NH_4Cl$; $MgSO_4 \times 7H_2O$ separately autoclaved)

The oxygen uptake rate (OUR) represents a suitable growth-coupled fermentation paremeter which is proportional both to the biomass and to the physiological condition of the culture.

If the algorithm indicated above is used with restriction of the OUR to 120 mmol/l·h (determined empirically), an optimally adjusted glycerol supply is achieved in the first growth phase. After reaching the intended value, the pump switches off as directed and the OUR falls.

After reaching the intended value, switching to a constant pump rate is carried out—this is taken care of by the above algorithm—and an optimum growth is achieved. In the case in which the maximum oxygen uptake rate is not reached, switching is carried out to the constant pump rate by said algorithm after a maximum in the oxygen uptake rate is passed through.

Figure 2:
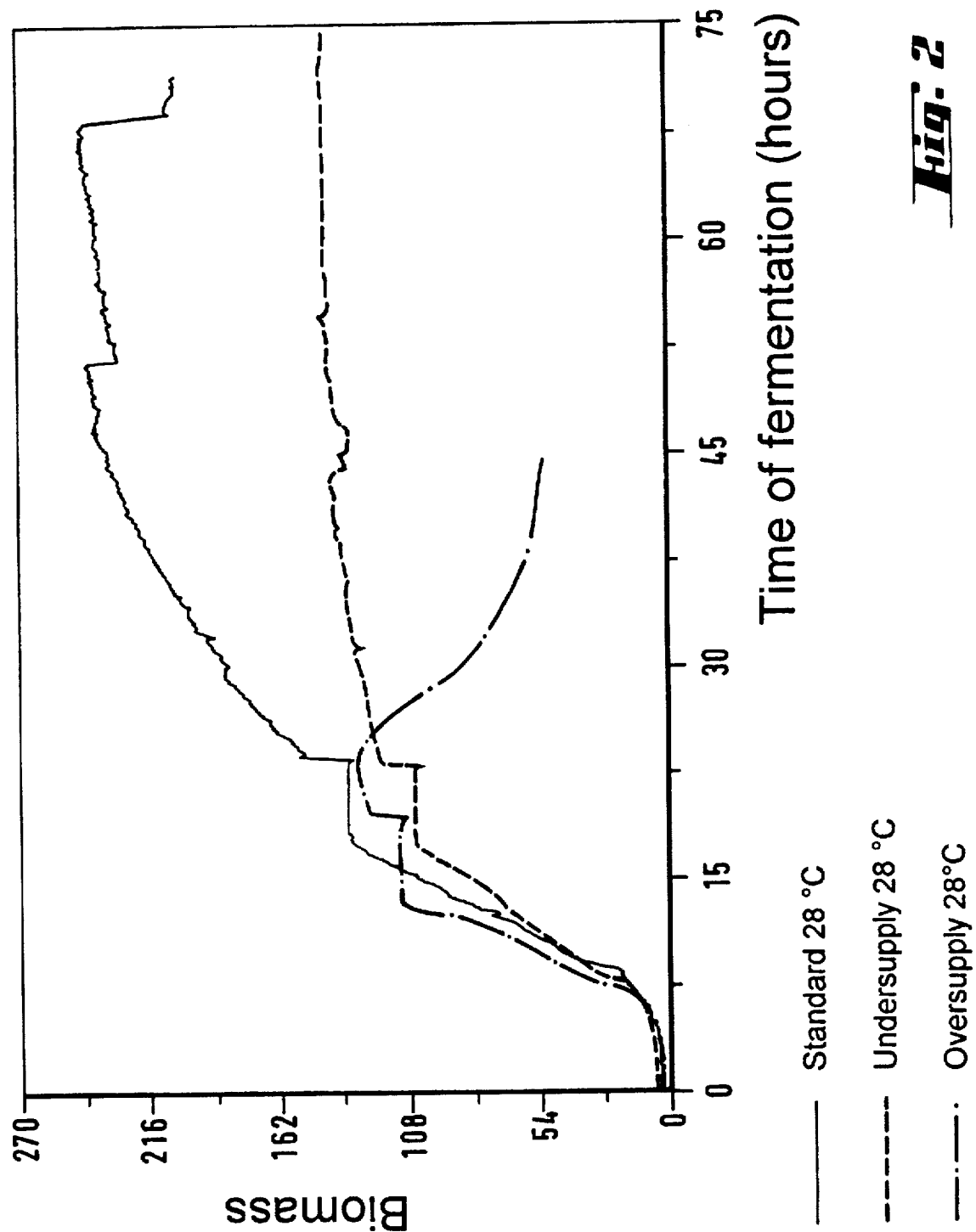

The results, which are shown in FIG. 1, FIG. 2 and Table 1, show that the fermentation proceeds automatically in an optimum manner with the aid of the process according to the invention, even if the conditions (in this case fermentation temperature, direct inoculation, undersupply) are changed. Only in the case of oversupply—which does not correspond to the procedure according to the present invention—does biomass production come to a halt. Table 2 shows that even with the strain DH 1 good biomass production can be achieved with low acetate formation.

TABLE 1

Organism W 3110 M:

| Conditions | Biomass (g/l) | Glycerol accumulation (mmol/l) | Acetate (mmol/l) |
| --- | --- | --- | --- |
| Standard | 231.0 | 0 | 4.7 |
| Undersupply | 139.1 | 0 | 5.8 |
| Oversupply | 56.4 | 674.0 | 491.0 |
| 25° C. | 227.0 | 0 | 4.7 |
| 33° C. | 169.0 | 0.5 | 7.5 |
| Direct inoculation | 196.0 | 0.8 | 6.2 |

TABLE 2

Various recipient strains of E. coli

| Strain | Biomass (g/l) | Glycerol accumulation (mmol/l) | Acetate (mmol/l) |
| --- | --- | --- | --- |
| W 3110 M | 231 | 0 | 4.7 |
| DH 1 | 175 | 0 | 5.2 |

We claim:

1. A process for the fermentation of an oxygen-dependent microorganism, which comprises:
    a) inoculating a fermentation broth with said oxygen-dependent microorganism;
    b) initially supplying a carbon source to said inoculated fermentation broth at a rate proportional to the oxygen uptake rate of said oxygen-dependent microorganism until a threshold value is reached, wherein said threshold value is that value at which no carbon oversupply takes place; and
    c) after the threshold value is reached, providing said carbon source to said inoculated fermentation broth at a constant supply until fermentation is finished.

2. The process for the fermentation of an oxygen-dependent microorganism as claimed in claim 1, wherein said oxygen-dependent microorganism is modified by genetic engineering to express a recombinant protein.

3. The process for the fermentation of an oxygen-dependent microorganism as claimed in claim 1, wherein said oxygen-dependent microorganism belongs to the species Escherichia coli.

4. The process for the fermentation of an oxygen-dependent microorganism as claimed in claim 3, wherein said oxygen-dependent microorganism is of the strain W 3110 M or DH 1.

5. The process for the fermentation of an oxygen-dependent microorganism as claimed in claim 1, wherein glutaryl acylase is produced.

6. The process for the fermentation of an oxygen-dependent microorganism as claimed in claim 1, wherein the inoculation of the microorganism in step (a) takes place by means of a preculture.

7. The process of the fermentation of an oxygen-dependent microorganism as claimed in claim 1, wherein the inoculation of the microorganism in step (a) takes place by a direct inoculation.

8. The process for the fermentation of an oxygen dependent microorganism as claimed in claim 1, wherein the supply of the carbon source takes place in a computer-controlled manner as a function of the oxygen uptake rate.

9. The process for the fermentation of an oxygen-dependent microorganism as claimed in claim 1, wherein the carbon source supplied to the microorganism is glycerol.

10. The process for the fermentation of an oxygen-dependent microorganism as claimed in claim 9, wherein said threshold value is that value at which no formation of acetate takes place.

11. The process as claimed in claim 1 wherein the oxygen uptake rate of step (b) and the carbon source supply of step (c) are determined empirically.

* * * * *